US007860694B2

(12) United States Patent
Ahn et al.

(10) Patent No.: US 7,860,694 B2
(45) Date of Patent: Dec. 28, 2010

(54) METHOD OF DESIGNING PROBES FOR DETECTING TARGET SEQUENCE AND METHOD OF DETECTING TARGET SEQUENCE USING THE PROBES

(75) Inventors: Tae-jin Ahn, Yongin-si (KR); Ji-young Oh, Yongin-si (KR); Jung-nam Lee, Yongin-si (KR); Jong-suk Chung, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 908 days.

(21) Appl. No.: 11/739,354

(22) Filed: Apr. 24, 2007

(65) Prior Publication Data

US 2008/0139398 A1 Jun. 12, 2008

(30) Foreign Application Priority Data

Aug. 17, 2006 (KR) ...................... 10-2006-0077826

(51) Int. Cl.
*G06F 17/10* (2006.01)
*G06G 7/58* (2006.01)

(52) U.S. Cl. ............................... 703/2; 702/19; 703/11; 435/6; 536/24.3; 211/41.12

(58) Field of Classification Search ....................... None
See application file for complete search history.

(56) References Cited

U.S. PATENT DOCUMENTS 7,013,221 B1 * 3/2006 Friend et al. .................. 702/20
2005/0033520 A1 * 2/2005 Dai et al. ...................... 702/19
2006/0183142 A1 8/2006 Choi et al.

FOREIGN PATENT DOCUMENTS

EP 1683872 A1 7/2006
JP 2004024247 1/2004
WO 9746711 A1 12/1997
WO 0111082 A2 2/2001

OTHER PUBLICATIONS

Guo, Z., et al.; "Enhanced discrimination of single nucleotide polymorphisms by artifical mismatch hybridization"; Nature Biotechnology; vol. 15; pp. 331-335; Apr. 15, 1997.

Troup, C.B., et al.; "Simulated Pharmacogenomics Excercises for the Cybertory(TM) Virtual Molecular Biology Laboratory"; Proceedings of the 2005 IEEE Computional Systems Bioinformatics Conference Workshops; 2005.

European Search Report dated Dec. 5, 2007 for Application No. 07102166.1 (all references cited in Search Report are listed above).

* cited by examiner

*Primary Examiner*—Carolyn L. Smith
(74) *Attorney, Agent, or Firm*—Cantor Colburn LLP

(57) ABSTRACT

A method of designing probes for detecting a target sequence and a method of detecting the target sequence using the probes are provided. The method of designing probes for detecting target sequence includes: selecting an anchoring location in the target sequence; selecting a first probe designing region; selecting a matched probe; and selecting a mismatched probe.

13 Claims, 9 Drawing Sheets

FIG. 1

|  | PROBE (SEQUENCE NO. 17) |
|---|---|
| SEQUENCE NO.1: ctahgagatcgggacgccagt | tttcgaaggagacgttgttg |
| SEQUENCE NO.2: ctaagagatcgggacgccagt | tttcgaaggagacgttgttg — TARGET SEQUENCE |
| SEQUENCE NO.3: cattgaagtcgggacgccagt | tttcgaCggagGcgttgttg |
| SEQUENCE NO.4: cattgacttcgggacgccagt | tttcgaaTgagGcgttgttg |
| SEQUENCE NO.5: ctawgaratcgggacgccagt | tttcgaTgagGcgttgttg |
| SEQUENCE NO.6: ctatgaaatcgggacgccagtag | tttcgGTggagGcgttgttg |
| SEQUENCE NO.7: ctacgagatcgggacgccagt | tttcgaTggagGcgttgttg |
| SEQUENCE NO.8: ctaggaatcatgcacgccagt | tGtATGaggagGcgttgttg |

Target row: ggatactaccctgttat

Non-target rows (SEQ 3–8): ggatactacc

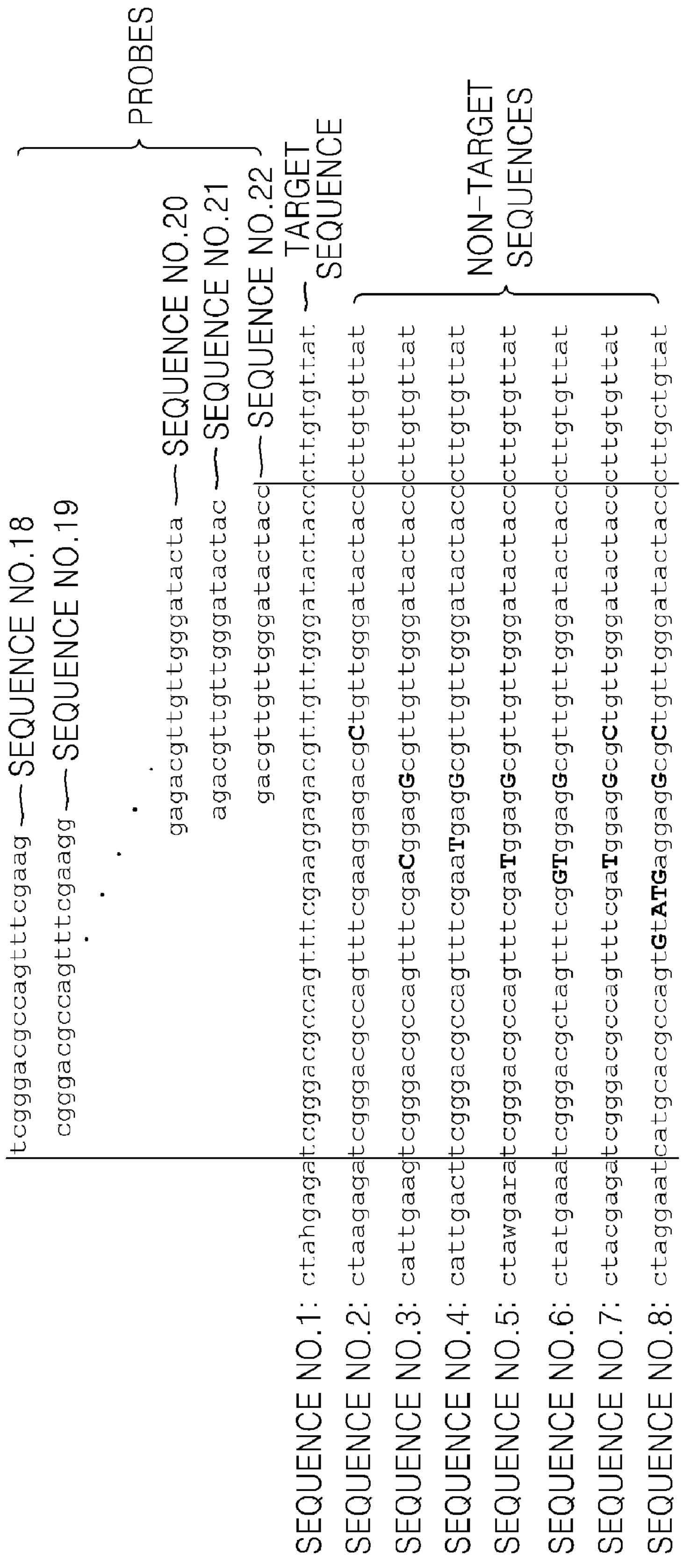

FIG. 2

```
SEQUENCE NO.1: ctahgagatcgggacgccagttttcgaag
SEQUENCE NO.2: ctaagagatcgggacgccagtttcgaaggagacgttgtgggatacta     — SEQUENCE NO.18
SEQUENCE NO.3: cattgaagtcgggacgccagtttcgaCggagcgttgttgggatactac    — SEQUENCE NO.19
SEQUENCE NO.4: cattgacttcgggacgccagtttcgaaTgagGcgttgttgggatactacc  ─ SEQUENCE NO.20 ⎫
SEQUENCE NO.5: ctawgaratcgggacgccagtttcgaTgagGcgttgttgggatactacc   ─ SEQUENCE NO.21 ⎬ PROBES
SEQUENCE NO.6: ctatgaaatcgggacgctagtttcGTgagGcgttgttgggatactacc    ─ SEQUENCE NO.22 ⎭
SEQUENCE NO.7: ctacgagatcgggacgccagtttcgaTgagCcgttgttgggatactacc        TARGET SEQUENCE
SEQUENCE NO.8: ctaggaatcatgcacgccagtGtATGagagGcgttgttgggatactacc   ⎫
                                                                    ⎬ NON-TARGET SEQUENCES
                                                                    ⎭
```

[REFERENCE DATA]

|  | | #1 | #2 | #3 | #4 |
|---|---|---|---|---|---|
| SAMPLE ONLY INCLUDING TARGET SEQUENCE → | pm | ● | ● | ● | ○ |
|  | mm | ● | ○ | ● | ● |

[EXPERIMENTAL DATA]

|  | | #1 | #2 | #3 | #4 |
|---|---|---|---|---|---|
| SAMPLE 1 → | pm | ● | ● | ● | ○ |
|  | mm | ● | ○ | ● | ● |

: TARGET SEQUENCE

|  | | #1 | #2 | #3 | #4 |
|---|---|---|---|---|---|
| SAMPLE 2 → | pm | ● | ● | ● | ● |
|  | mm | ● | ○ | ● | ● |

: TARGET SEQUENCE + α

|  | | #1 | #2 | #3 | #4 |
|---|---|---|---|---|---|
| SAMPLE 3 → | pm | ● | ○ | ○ | ○ |
|  | mm | ● | ○ | ● | ● |

: TARGET SEQUENCE X

```
SEQUENCE LISTING

<160> NUMBER OF SEQ ID NOS: 27

<210> SEQ ID NO 1
<211> LENGTH: 60
<212> TYPE: DNA
<213> ORGANISM: Streptococcus oralis

<400> SEQUENCE: 1

ctahgagatc gggacgccag tttcgaagga gacgttgttg ggatactacc cttgtgttat     60


<210> SEQ ID NO 2
<211> LENGTH: 60
<212> TYPE: DNA
<213> ORGANISM: Streptococcus pneumoniae

<400> SEQUENCE: 2

ctaagagatc gggacgccag tttcgaagga gacgctgttg ggatactacc cttgtgttat     60


<210> SEQ ID NO 3
<211> LENGTH: 60
<212> TYPE: DNA
```

-continued

<213> ORGANISM: Streptococcus dysgalactiae

<400> SEQUENCE: 3
cattgaagtc gggacgccag tttcgacgga ggcgttgttg ggatactacc cttgtgttat 60

<210> SEQ ID NO 4
<211> LENGTH: 60
<212> TYPE: DNA
<213> ORGANISM: Streptococcus pyogenes

<400> SEQUENCE: 4
cattgacttc gggacgccag tttcgaatga ggcgttgttg ggatactacc cttgtgttat 60

<210> SEQ ID NO 5
<211> LENGTH: 60
<212> TYPE: DNA
<213> ORGANISM: Streptococcus sanguis

<400> SEQUENCE: 5
ctawgaratc gggacgccag tttcgatgga ggcgttgttg ggatactacc cttgtgttat 60

<210> SEQ ID NO 6
<211> LENGTH: 60
<212> TYPE: DNA
<213> ORGANISM: Streptococcus bovis

<400> SEQUENCE: 6
ctatgaaatc gggacgctag tttcggtgga ggcgttgttg ggatactacc cttgtgttat 60

<210> SEQ ID NO 7
<211> LENGTH: 60
<212> TYPE: DNA
<213> ORGANISM: Streptococcus gordonii

<400> SEQUENCE: 7
ctacgagatc gggacgccag tttcgatgga ggcgctgttg ggatactacc cttgtgttat 60

<210> SEQ ID NO 8
<211> LENGTH: 60
<212> TYPE: DNA
<213> ORGANISM: Gemella melitensis

<400> SEQUENCE: 8
ctaggaatca tgcacgccag tgtatgagga ggcgctgttg ggatactacc cttgctgtat 60

<210> SEQ ID NO 9
<211> LENGTH: 17
<212> TYPE: DNA
<213> ORGANISM: Artificial Sequence
<220> FEATURE:
<223> OTHER INFORMATION: probe

<400> SEQUENCE: 9
agtttcgaag gagacgt 17

<210> SEQ ID NO 10
<211> LENGTH: 25
<212> TYPE: DNA
<213> ORGANISM: Artificial Sequence
<220> FEATURE:
<223> OTHER INFORMATION: probe

<400> SEQUENCE: 10
agtttcgaag gagacgtagt tggga 25

-continued

<210> SEQ ID NO 11
<211> LENGTH: 17
<212> TYPE: DNA
<213> ORGANISM: Artificial Sequence
<220> FEATURE:
<223> OTHER INFORMATION: probe

<400> SEQUENCE: 11
gtttcgaagg agacgtt 17

<210> SEQ ID NO 12
<211> LENGTH: 25
<212> TYPE: DNA
<213> ORGANISM: Artificial Sequence
<220> FEATURE:
<223> OTHER INFORMATION: probe

<400> SEQUENCE: 12
gtttcgaagg agacgttctt gggat 25

<210> SEQ ID NO 13
<211> LENGTH: 17
<212> TYPE: DNA
<213> ORGANISM: Artificial Sequence
<220> FEATURE:
<223> OTHER INFORMATION: probe

<400> SEQUENCE: 13
cgaaggagac gttgttg 17

<210> SEQ ID NO 14
<211> LENGTH: 25
<212> TYPE: DNA
<213> ORGANISM: Artificial Sequence
<220> FEATURE:
<223> OTHER INFORMATION: probe

<400> SEQUENCE: 14
cgaaggagac gttgttgcga tacta 25

<210> SEQ ID NO 15
<211> LENGTH: 17
<212> TYPE: DNA
<213> ORGANISM: Artificial Sequence
<220> FEATURE:
<223> OTHER INFORMATION: probe

<400> SEQUENCE: 15
aggagacgtt gttggga 17

<210> SEQ ID NO 16
<211> LENGTH: 25
<212> TYPE: DNA
<213> ORGANISM: Artificial Sequence
<220> FEATURE:
<223> OTHER INFORMATION: probe

<400> SEQUENCE: 16
aggagacgtt gttgggaaac taccc 25

<210> SEQ ID NO 17
<211> LENGTH: 20
<212> TYPE: DNA
<213> ORGANISM: Artificial Sequence
<220> FEATURE:

-continued

<223> OTHER INFORMATION: probe

<400> SEQUENCE: 17
tttcgaagga gacgttgttg 20

<210> SEQ ID NO 18
<211> LENGTH: 20
<212> TYPE: DNA
<213> ORGANISM: Artificial Sequence
<220> FEATURE:
<223> OTHER INFORMATION: probe

<400> SEQUENCE: 18
tcgggacgcc agtttcgaag 20

<210> SEQ ID NO 19
<211> LENGTH: 20
<212> TYPE: DNA
<213> ORGANISM: Artificial Sequence
<220> FEATURE:
<223> OTHER INFORMATION: probe

<400> SEQUENCE: 19
cgggacgcca gtttcgaagg 20

<210> SEQ ID NO 20
<211> LENGTH: 20
<212> TYPE: DNA
<213> ORGANISM: Artificial Sequence
<220> FEATURE:
<223> OTHER INFORMATION: probe

<400> SEQUENCE: 20
gagacgttgt tgggatacta 20

<210> SEQ ID NO 21
<211> LENGTH: 20
<212> TYPE: DNA
<213> ORGANISM: Artificial Sequence
<220> FEATURE:
<223> OTHER INFORMATION: probe

<400> SEQUENCE: 21
agacgttgtt gggatactac 20

<210> SEQ ID NO 22
<211> LENGTH: 20
<212> TYPE: DNA
<213> ORGANISM: Artificial Sequence
<220> FEATURE:
<223> OTHER INFORMATION: probe

<400> SEQUENCE: 22
gacgttgttg ggatactacc 20

<210> SEQ ID NO 23
<211> LENGTH: 17
<212> TYPE: DNA
<213> ORGANISM: Artificial Sequence
<220> FEATURE:
<223> OTHER INFORMATION: probe

<400> SEQUENCE: 23
ttgttgggat actaccc 17

-continued

```
<210> SEQ ID NO 24
<211> LENGTH: 17
<212> TYPE: DNA
<213> ORGANISM: Artificial Sequence
<220> FEATURE:
<223> OTHER INFORMATION: probe

<400> SEQUENCE: 24

gttgttggga tactacc                                                    17


<210> SEQ ID NO 25
<211> LENGTH: 17
<212> TYPE: DNA
<213> ORGANISM: Artificial Sequence
<220> FEATURE:
<223> OTHER INFORMATION: probe

<400> SEQUENCE: 25

tttcgaagga gacgttg                                                    17


<210> SEQ ID NO 26
<211> LENGTH: 17
<212> TYPE: DNA
<213> ORGANISM: Artificial Sequence
<220> FEATURE:
<223> OTHER INFORMATION: probe

<400> SEQUENCE: 26

gtttcgaagg agacgtt                                                    17


<210> SEQ ID NO 27
<211> LENGTH: 17
<212> TYPE: DNA
<213> ORGANISM: Artificial Sequence
<220> FEATURE:
<223> OTHER INFORMATION: probe

<400> SEQUENCE: 27

agtttcgaag gagacgt                                                    17
```

METHOD OF DESIGNING PROBES FOR DETECTING TARGET SEQUENCE AND METHOD OF DETECTING TARGET SEQUENCE USING THE PROBES

This application claims the benefit of Korean Patent Application No. 10-2006-0077826, filed on Aug. 17, 2006, the disclosure of which is incorporated herein in its entirety by reference.

BACKGROUND OF THE INVENTION

1. Field of the Invention

The present invention relates to a method of designing probes for detecting a target sequence and a method of detecting a target sequence using the probes.

2. Description of the Related Art

Due to recent advances in biotechnology, genomic sequences of many species, including humans, have been identified. Consequently, research on making a microarray for sequence analysis and disease diagnosis has been widely conducted. A microarray comprises a substrate on which a group of polynucleotides are immobilized at high density, wherein each group of polynucleotides is immobilized at fixed locations. A microarray can be used to analyze a target biomolecule to obtain a large amount of biological information (for example, sequence), while requiring a minimal amount of the target biomolecule, such as a nucleic acid or a protein.

For example, when a polynucleotide (also called "a probe", "a probe nucleic acid", or "a probe polynucleotide") is immobilized on the microarray that can be specifically hybridized with a target nucleic acid sequence, the microarray can be used to detect and identify the target nucleic acid sequence.

FIG. 1 is a schematic diagram illustrating an example of a conventional method of designing probes.

Referring to FIG. 1, in this conventional method of designing a probe, one desirable probe sequence is selected that can specifically hybridize with the complement of the shown target sequence, but does not cross-hybridize with other non-target sequences. However, it is difficult to design a specific probe when sequence similarity between the target sequence and non-target sequences is high or when the number of target sequences to be identified by the probe is large.

For example, in order to identify a species of bacteria in a sample comprising a plurality of bacteria, a consensus sequence of the plurality of bacteria, for example, a consensus sequence from 16S rRNA or 23S rRNA, can be used to identify probes specific for the various bacterial species in the sample. Such a method can be used to identify several species of bacteria, but is limited to identification of ten or fewer species of bacteria in a given sample since sequence similarity is remarkably high.

FIG. 2 is a schematic diagram illustrating another example of a conventional method of designing probes.

Referring to FIG. 2, in this second conventional method of designing a probe, all possible probes of a given length which hybridize with the complement of the target sequence shown are selected. The sequences of the probes of a given length are varied by varying the position of the first nucleotide of each probe relative to the target region shown in SEQ ID NO:1. As can be seen in FIG. 2, each probe sequence starts 1 bp further 3' along SEQ ID NO:1. However, a microarray of probes designed using this method would be expensive to manufacture and would yield results that are difficult and time-consuming to analyze since a large number of probes are used in this method.

SUMMARY OF THE INVENTION

The present invention provides a method of designing probes for detecting a target sequence to rapidly and accurately detect the presence of the target sequence in reaction samples containing the target sequence and a large number of non-target sequences.

In one embodiment, the method comprises selecting an anchoring location in a target sequence, wherein the anchoring location is a location in the target sequence at which a first non-target sequence in a plurality of non-target sequences is different from the target sequence, wherein the first non-target sequence has a sequence similarity to the target sequence that is identical to or higher than the sequence similarity of other non-target sequences in the plurality of non-target sequences; selecting a first probe designing region, wherein the first probe designing region is a fixed region in the target sequence comprising the anchoring location; selecting a probe selection location, wherein the probe selection location is a location in the target sequence at which a second non-target sequence in the plurality of non-target sequences is different from the target sequence; selecting a matched probe, wherein the matched probe comprises a sequence complementary to the target sequence, wherein the probe selecting location is at the center of the sequence of the matched probe; and selecting a mismatched probe, wherein the mismatched probe is longer than the matched probe, wherein the mismatched probe comprises a sequence complementary to the target sequence at all locations except at a mismatched location, wherein the probe selection location is at a first location in the sequence of the mismatched probe and the mismatched location is at a second location in the sequence of the mismatched probe.

According to another aspect of the present invention, there is provided a method of detecting a target sequence. The method comprises: contacting a sample comprising a DNA sequence with a matched probe and a mismatched probe designed by the method described above to detect a target sequence; and detecting a hybridization reaction between the matched probe or the mismatched probe and the DNA sequence present in the sample. The invention further provides a method of manufacturing a microarray comprising immobilized probes selected by the above-described method.

The present invention also provides a computer readable recording medium having recorded thereon a program for causing a computer to perform the method of designing probes for detecting target sequence.

BRIEF DESCRIPTION OF THE DRAWINGS

The above and other features and advantages of the present invention will become more apparent by describing in detail exemplary embodiments thereof with reference to the attached drawings in which:

FIG. 1 is a schematic diagram illustrating an example of a conventional method of designing probes;

FIG. 2 is a schematic diagram illustrating another example of a second conventional method of designing probes;

DETAILED DESCRIPTION OF THE INVENTION

Hereinafter, the present invention will be described more fully with reference to the accompanying drawings, in which exemplary embodiments of the invention are shown.

Figure 3:
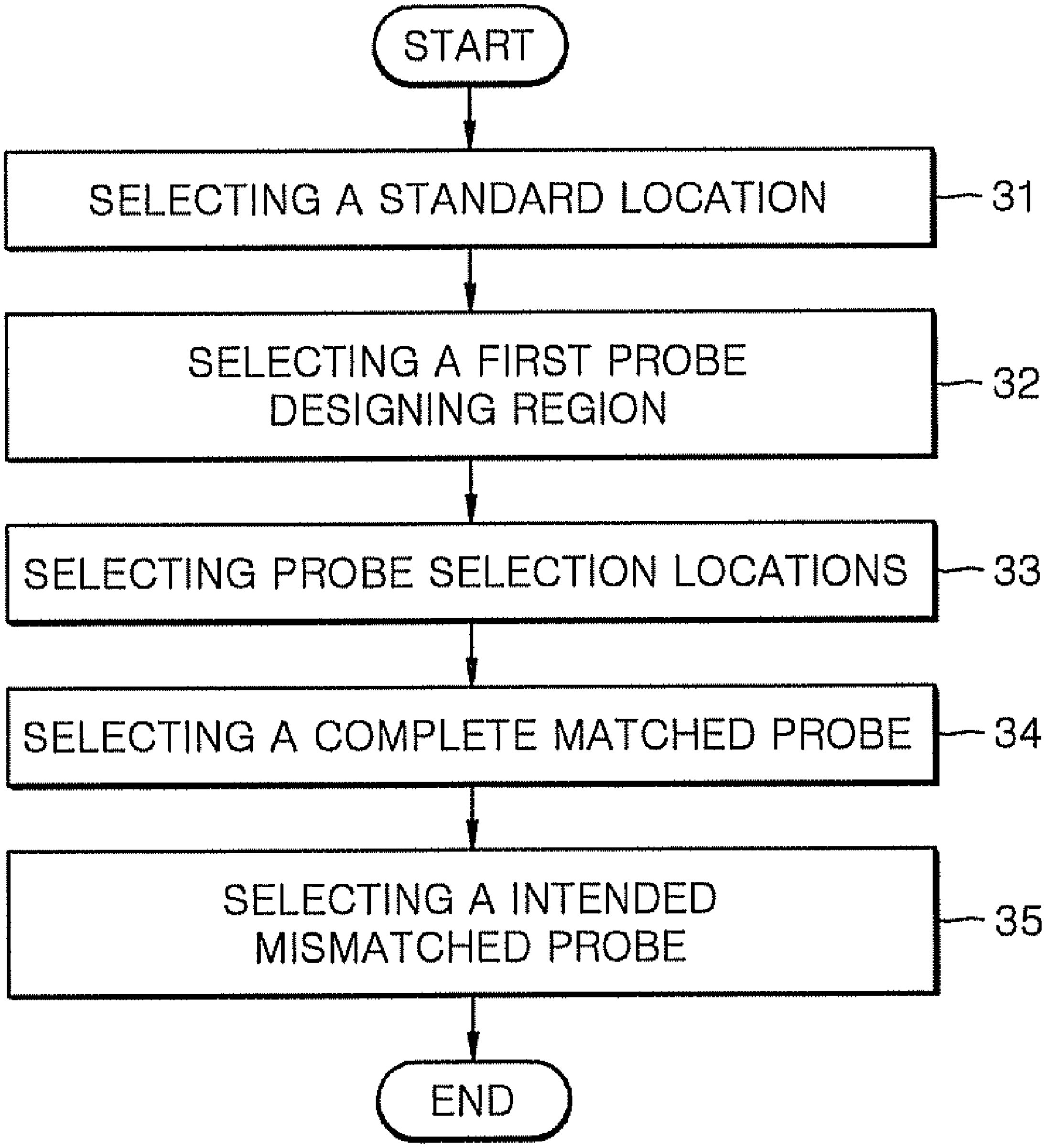
FIG. 3 is a flowchart illustrating a method of designing probes for detecting target sequence according to an embodiment of the present invention.

FIG. 3 is a flowchart illustrating a method of designing probes for detecting a target sequence according to an embodiment of the present invention.

Referring to FIG. 3, the method of designing probes for detecting a target sequence comprises selecting an anchoring location 31, selecting a first probe designing region 32, selecting a probe selection location 33, selecting a matched probe 34, and selecting a mismatched probe 35.

In selecting of the anchoring location 31, a location in the target sequence where a non-target sequence having the highest sequence similarity with the target sequence differs from the target sequence is selected as the anchoring location.

As used herein, the term "target sequence" refers to a polynucleotide selected to be detected by binding to a probe. Examples of a target sequence include genome DNA, a DNA fragment cleaved by a restriction enzyme, and a PCR product. A genome DNA fragment obtained by amplifying a specific region of genome DNA through a polymerase chain reaction (PCR) is another example of a commonly used target sequence.

As used herein, the term "non-target sequence" refers to all sequences other than the target sequence contained in a reaction sample. In the present invention, the case when the target sequence and the non-target sequences have very high sequence similarity is particularly considered.

Figure 4A:
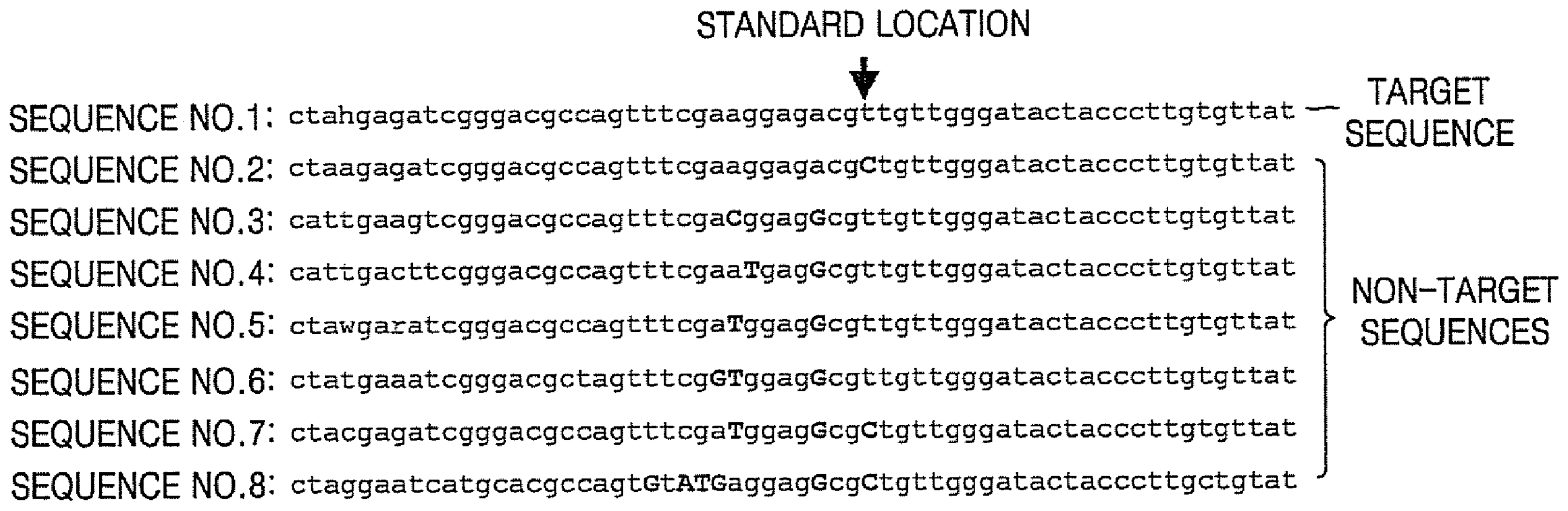
FIG. 4A is a schematic diagram illustrating an example of selecting an anchoring location according to an embodiment of the present invention.

FIG. 4A is a schematic diagram illustrating an example of selecting an anchoring location according to an embodiment of the present invention.

Referring to FIG. 4A, a target sequence to be detected (SEQ ID NO: 1) and 7 non-target sequences (SEQ ID NOs: 2 through 8) are shown. Upon comparison of the target sequence and the non-target sequences, the non-target sequence with SEQ ID NO: 2 varies from the target sequence at only 1 bp, the non-target sequences with SEQ ID NOs: 3 through 5 vary from the target sequence at 2 bp, the non-target sequences with SEQ ID NOs: 6 and 7 vary from the target sequence at 3 bp, and the non-target sequence with SEQ ID NO: 8 varies from the target sequence at 6 bp. Therefore, the non-target sequence with SEQ ID NO: 2 has the highest sequence similarity with the target sequence since there is only one bp at which the sequences differ (indicated by the arrow). At that position, the target sequence has the nucleotide t while the non-target sequence with SEQ ID NO: 2 has the nucleotide c. This location in the target sequence is selected as the anchoring location.

Figure 4B:
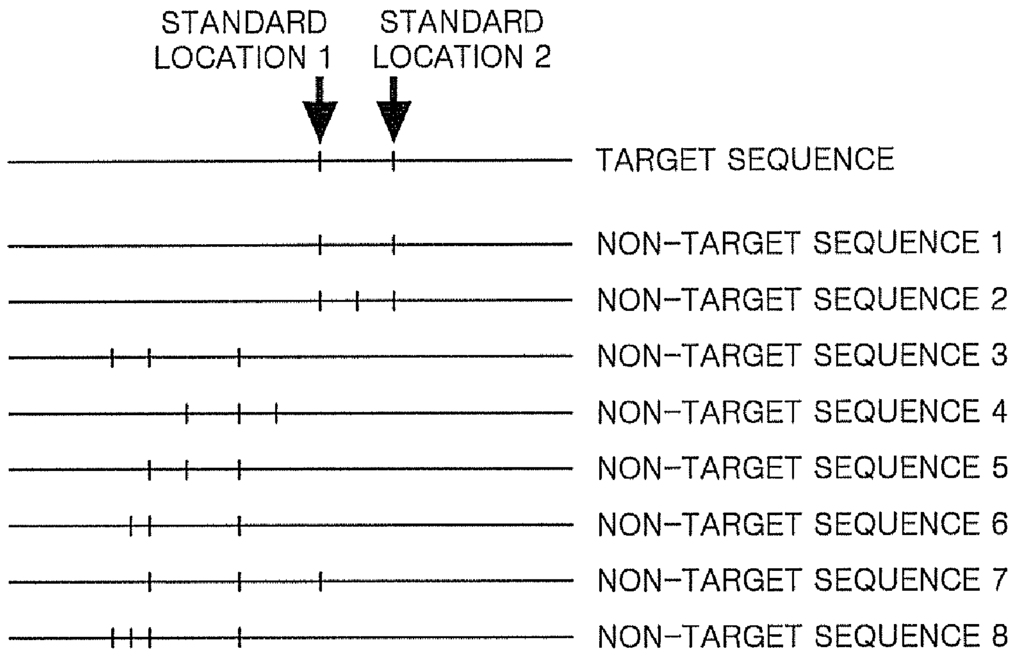
FIG. 4B is a schematic diagram illustrating another example of selecting an anchoring location according to an embodiment of the present invention.

FIG. 4B is a schematic diagram illustrating another example of selecting an anchoring location according to an embodiment of the present invention. Referring to FIG. 4B, non-target sequence 1 has the highest homology with the target sequence since there are only two different locations that differ from the target sequence 1.

When 2 or more locations exist in the target sequence at which the non-target sequence with the highest sequence similarity differs from the target sequence, any one of the locations can be selected as an anchoring location.

As illustrated in FIG. 4B, either one of the 2 locations identified by alignment of the target sequence with non-target sequence 1 can be selected as an anchoring location.

Figure 4C:
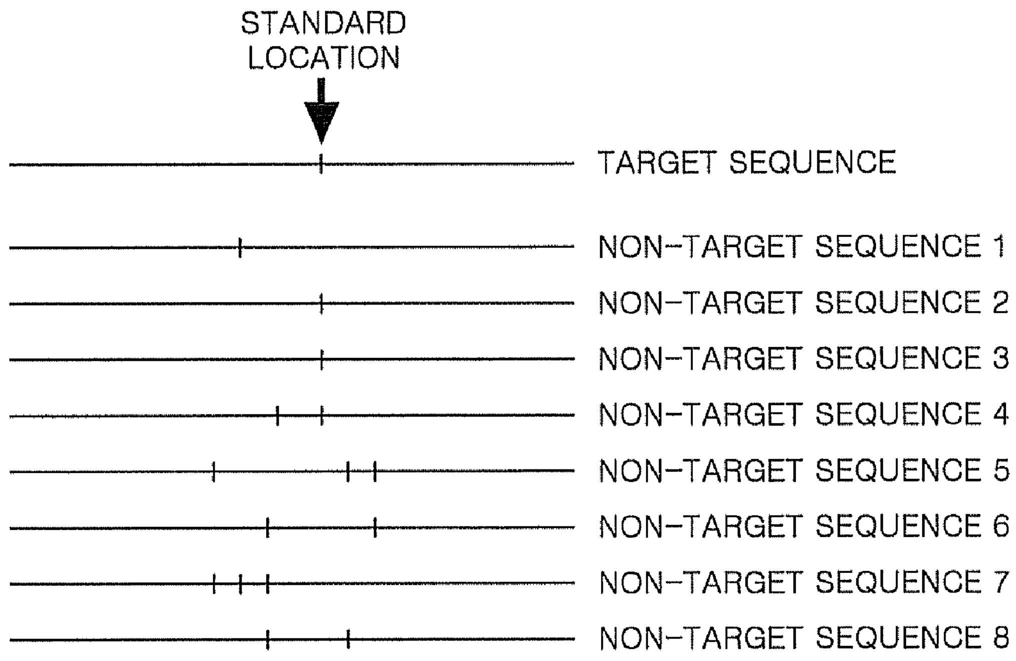
FIG. 4C is a schematic diagram illustrating yet another example of selecting an anchoring location according to an embodiment of the present invention.

FIG. 4C is a schematic diagram illustrating yet another example of selecting an anchoring location according to an embodiment of the present invention.

Referring to FIG. 4C, multiple non-target sequences having the highest sequence similarity to the target sequence. Non-target sequences 1, 2, and 3 each differ from the target sequence at a single location, however the three non-target sequences do not differ from the target sequence at the same location. As can be seen in FIG. 4C, non-target sequence 1 is different from the target sequence at one location in the target sequence 1 (group 1) while non-target sequences 2 and 3 (group 2) are different from the target sequence at a different location in the target sequence. Because non-target sequences 2 and 3 differ from the target sequence at the same location in the target sequence, they are grouped (group 2). In this example groups 1 and 2 have the same degree of homology with the target sequence (only 1 location of difference), however the locations of variation from the target sequence have different frequencies of occurrence in the pool of sequences. In this case, the location of variation in the target sequence having the highest frequency (the location characterizing group 2) is selected as the anchoring location.

On the other hand, when 2 or more groups of non-target sequences having the highest sequence similarity to the target sequence exist in the pool of non-target sequences, and the locations of variation from the target sequence of all groups have the same frequency of occurrence in the pool of non-target sequences, then any one of the locations of variation can be selected as an anchoring location.

Regarding selecting of the first probe designing region 32, the first probe designing region is a fixed region in the target sequence including the anchoring location. All probes designed from the sequence of the fixed region have a fixed length and include the anchoring location in their sequence.

The first probe designing region may be represented by Formula 1.

$$i-n+1 \leqq \text{first probe designing region} \leqq i+n-1 \qquad \text{<Formula 1>}$$

wherein i is the anchoring location and n is the length of the probe.

Figure 5:
FIG. 5 is a schematic diagram illustrating an example of selecting a first probe designing region according to an embodiment of the present invention.

FIG. 5 is a schematic diagram illustrating an example of selecting a first probe designing region according to an embodiment of the present invention.

A probe having the same sequence as the target sequence shown in the figure can hybridize with the complement of the target sequence.

Referring to FIG. 5, the length of the probe to be designed is set to 17 bp. When n=17 and i=0 are introduced in Formula 1, the first probe designing region is in a range of −16 to 16 relative to the anchoring location. In this instance, the maximum number of probes of n=17 that could be designed in this first probe designing region is 17. Each of these possible probes designed in the first probe designing region would include the anchoring location.

Regarding the step of selecting the probe selection locations 33, a second probe designing region is selected in the target sequence. The probe selection locations are within the second probe designing region of the target sequence and are selected based on the locations in the target sequence at which the non-target sequences in the sequence pool differ from the target sequence.

For the example shown in FIG. 5, the second probe designing region of the target sequence is within the range of the sequence corresponding to the center portion of probe 1 and the center portion of probe 17.

In general, the second probe designing region of the target sequence may be represented by Formula 2, when the length of the probe is an odd number, and may be represented by Formula 3, when the length of the probe is an even number.

$$i-(n-1)/2 \leqq \text{second probe designing region} \leqq i+(n-1)/2 \quad \text{<Formula 2>}$$

$$i-n/2+1 \leqq \text{second probe designing region} \leqq i+n/2-1 \quad \text{<Formula 3>}$$

wherein, i is the anchoring location and n is the length of the probe to be designed.

Since a probe selection location is selected within the second probe designing region, a matched probe will include the anchoring location.

Figure 6:
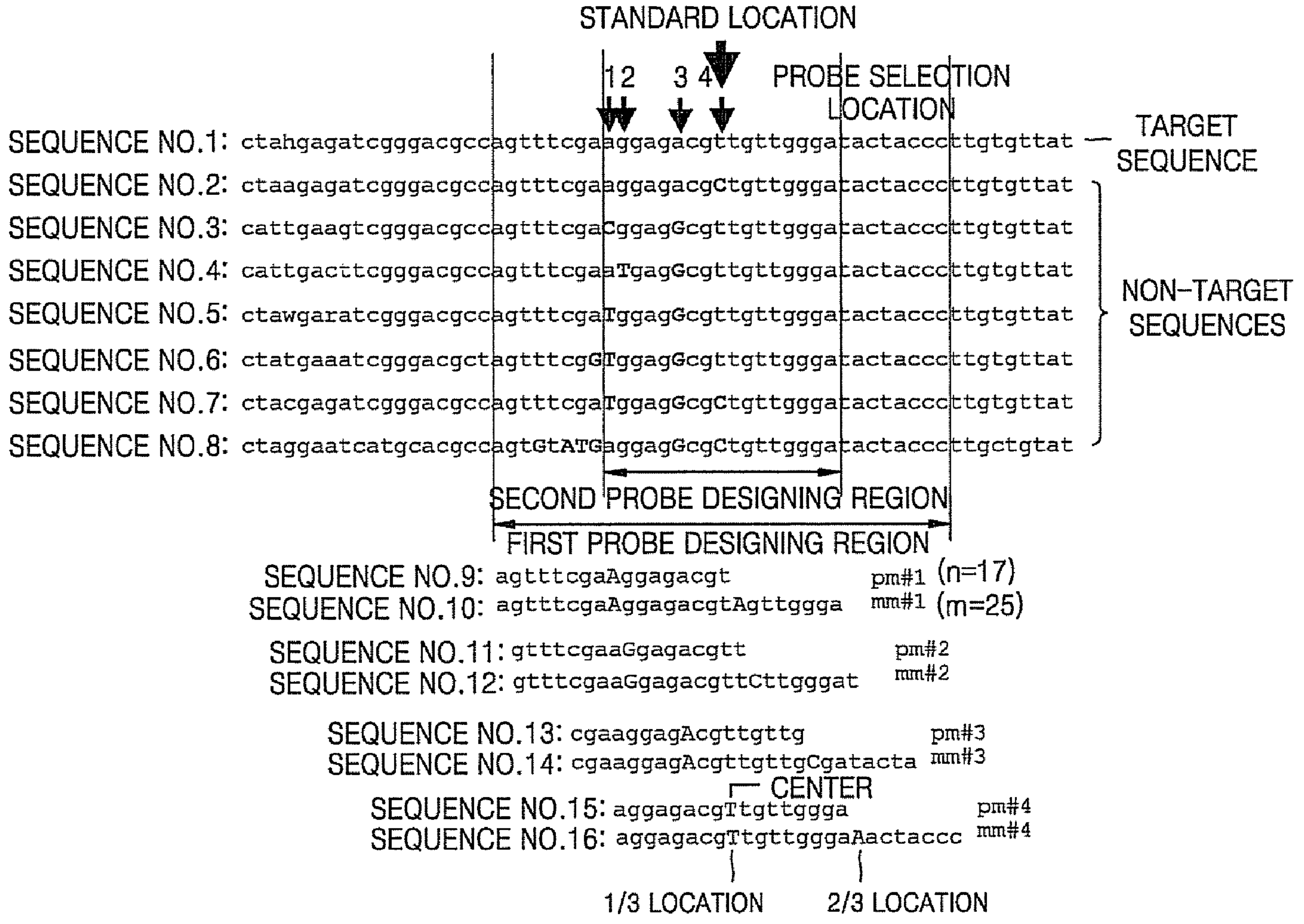
FIG. 6 is a schematic diagram illustrating an example of selecting a probe selection location, selecting a completely matched probe, and a selecting a mismatched probe.

FIG. 6 is a schematic diagram illustrating an example of selecting a probe selection location, selecting a matched probe, and selecting a mismatched probe.

Shown in FIG. 6 is the second probe designing region when length of the probe is set to 17 (n=17). Also illustrated in FIG. 6 are probe selection locations 1 through 4, which are selected by identifying locations in the second probe designing region of the target sequence at which one or more of the non-target sequences in the sequence pool differ from the target sequence.

In the selecting of the matched probe 34, a matched probe is selected to include a probe selection location at the center of its sequence and to have a sequence completely complementary to the complement of the target sequence (i.e, in terms of the target sequence shown in FIG. 6, the probe sequence would have a sequence identical to SEQ ID NO:1, with one of the four probe selection locations at its center).

When the length of a matched probe, n, is an odd number, the center of the matched probe is at the (n+1)/2 th position of the probe sequence. When the length of a matched probe, n, is an even number, the center of the matched probe is considered to be either of the n/2 th or the n/2+1 th position of the probe sequence.

Regarding selecting of a mismatched probe 35, a mismatched probe is selected to be longer than a matched probe, to include a probe selection location at a first location, and to include a mismatched nucleotide at a second location but to otherwise be formed of a sequence identical to the shown target sequence.

The first location may be at ⅓ of the mismatched probe and the second location may be at ⅔ of the mismatched probe.

When the direction is set from 5' to 3', the first and second locations may be at ⅓ and ⅔ of the mismatched probe, respectively, or may be at ⅔ and ⅓ of the mismatched probe.

When the length of the mismatched probe, m, is a multiple of 3, the locations corresponding to ⅓ and ⅔ of the mismatched probe are the m/3 th and the 2 m/3+1 th positions of the mismatched probe sequence, respectively. When the length of the intended mismatched probe, m, is a multiple of 3+1 or a multiple of 3+2, m/3 will not be an integer. In these two instances, only the integer is accepted for the value of m/3; herein, this is referred to as the "descending value of m/3". For example, when m/3=3.33, the integer 3 is used and the 0.33 is discarded or when m/3=3.67, only the 3 is used and the 0.67 is discarded. The locations corresponding to ⅓ and ⅔ of the mismatched probe are then the descending order of m/3 and (descending value of m/3)×2+1 th positions, respectively or (descending value of m/3)+1st and (descending value of m/3)×2+2 th positions, respectively. When a length of the mismatched probe m is a multiple of 3+2, locations where ⅓ and ⅔ of the mismatched probe may be (descending value of m/3)+1st and (descending value of m/3)×2+2 nd positions, respectively.

In some embodiments, the length of a matched probe is 17 to 25 bp and the length of a mismatched probe is 25 to 36 bp, but the lengths are not limited thereto. In general, the length of a matched probe is ⅔ times the length of a corresponding mismatched probe.

Referring to FIG. 6, a matched probe (pm) and a mismatched probe (mm) are designed with respect to each of the probe selection locations 1 through 4. The length of the matched probes (pm), n, and the length of the mismatched probe (mm), m, are set to 17 and 25, respectively.

For example, consider matched and mismatched probes designed with respect to probe selection location 4. The matched probe (pm #4) (sequence No. 15) includes the probe selection location 4 at its center and is formed of a sequence identical to the shown target sequence so that it can completely hybridize with the complement of the shown target sequence. In addition, the mismatched probe (mm #4) (SEQ ID NO: 16) includes the probe selection location 4 at a location corresponding to ⅓ of the length of the intended mismatched probe (mm #4) (SEQ ID NO: 16) and includes a mismatched nucleotide at a location corresponding to ⅔ of its length but is otherwise formed of a sequence identical to the shown target sequence. The nucleotide in the target sequence corresponding to the probe selection location at ⅓ of the mismatched probe (mm #4) is T and the nucleotide in the target sequence corresponding to the mismatch location at ⅔ of the mismatched probe (mm #4) is T. Therefore, the mismatched nucleotide at ⅔ of the mismatched probe (mm #4) can be anything but T (i.e., A, C, or G), and in the mismatched probe (mm #4) the mismatched nucleotide is A. Similarly for the mismatched probe designed with respect to probe selection location 1 (mm #1), the nucleotide in the target sequence corresponding to the probe selection location at ⅓ of the mismatched probe (mm #1) is A and the nucleotide in the target sequence corresponding to the mismatch location at ⅔ of the mismatched probe (mm #1) is T. Therefore, the mismatched nucleotide at ⅔ of the mismatched probe (mm #1) i may be anything but T (i.e., A, C, or G).

Embodiments of the present invention also relate to an apparatus for performing these operations. This apparatus may be specially designed and/or constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. Certain embodiments of the present invention employ processes acting under control of instructions or data stored in or transferred through one or more computer systems.

The method of designing probes for detecting a target sequence in a reaction sample comprising the target sequence and a plurality of non-target sequences according to an embodiment of the present invention can be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

Examples of program instructions (computer readable codes) include both machine code, such as produced by a compiler, and files containing higher level code that may be executed by the computer using an interpreter. Further, the program instructions include machine code, source code and any other code that directly or indirectly controls operation of a computing machine in accordance with this invention. The code may specify input, output, calculations, conditionals, branches, iterative loops, etc.

The invention also provides a microarray for detecting a target sequence. The microarray is manufactured by immobilizing matched and mismatched probes designed by the method disclosed herein on a substrate.

The microarray may be manufactured using the probes according to a typical method known to those skilled in the art. For example, the substrate can be coated with an active group selected from the group consisting of aminosilane, poly-L-lysine, and aldehyde. The substrate can be a silicon wafer, glass, quartz, metal, or plastic. The probe set may be immobilized on the substrate using a piezoelectric micropipetting method, a pin-shaped spotter, etc.

Figure 7:
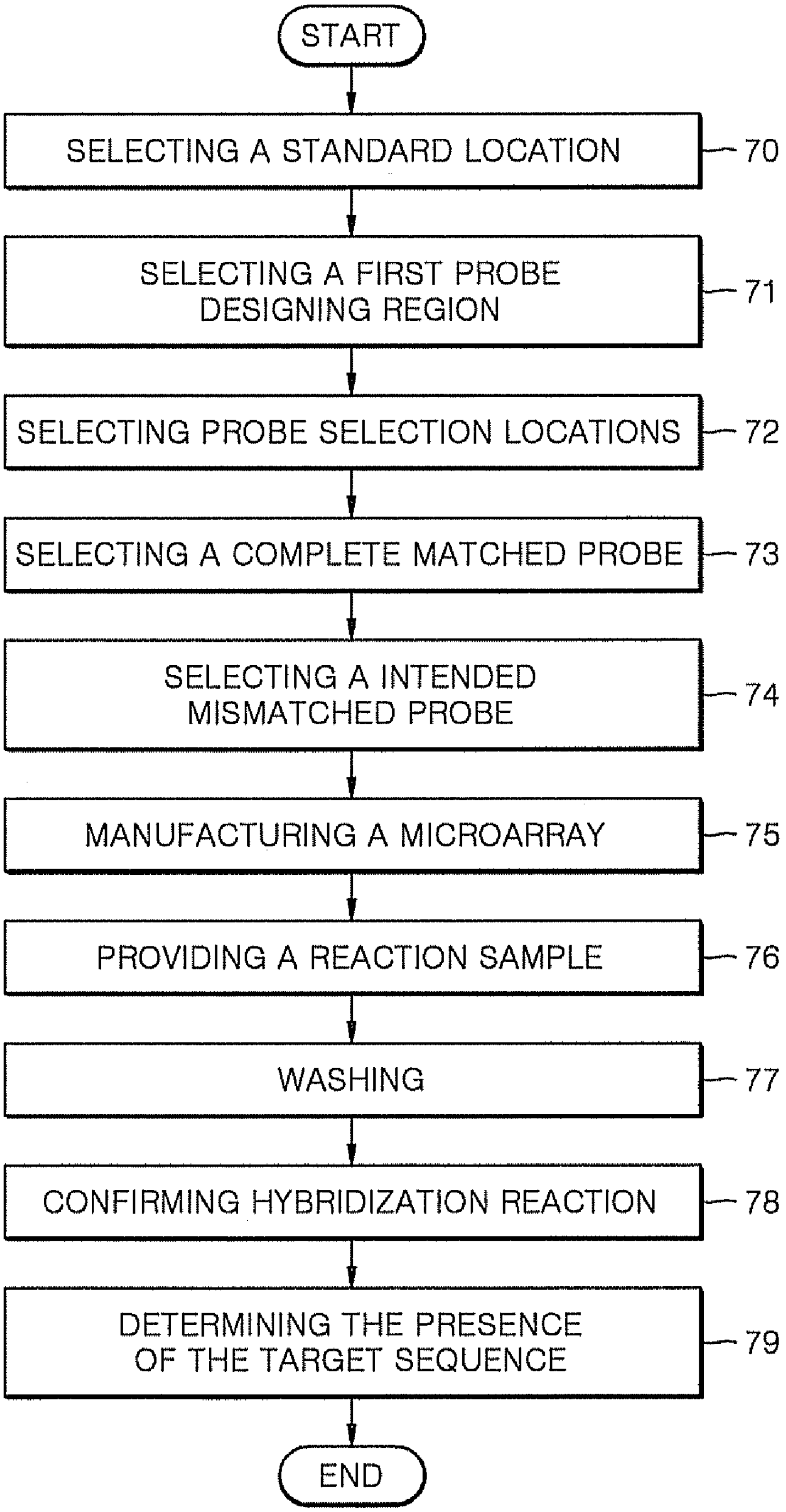
FIG. 7 is a flowchart of a method of detecting a target sequence according to an embodiment of the present invention.

FIG. 7 is a flowchart of the method of detecting a target sequence according to an embodiment of the present invention.

Referring to FIG. 7, the method of detecting target sequence includes selecting an anchoring location 70, selecting a first probe designing region 71, selecting probe selection locations 72, selecting a matched probe 73, selecting a mismatched probe 74, manufacturing a microarray 75, contacting a sample to a matched probe and a mismatched probe, washing 77, detecting a hybridization reaction 78, and determining the presence of the target sequence 79.

The operation of selecting the anchoring location 70, selecting the first probe designing region 71, selecting the probe selection locations 72, selecting the matched probe 73, and selecting the mismatched probe 74 are as described above for the method of designing probes for detecting a target sequence and thus a detailed description thereof is omitted.

In manufacturing of the microarray 75, the matched probe and the mismatched probe designed above are fixed onto a substrate to manufacture a microarray for detecting the target sequence. The microarray comprising the matched and mismatched probes may be manufactured according to any method known to those skilled in the art. That is, the substrate may be coated with an active group selected from the group consisting of an amino-silane, poly-L-lysine, and an aldehyde. The substrate may be a silicon wafer, glass, quartz, metal, or a plastic. The probe set may be immobilized on the substrate using a piezoelectric micropipetting method, a pin-shaped spotter, etc.

In the providing of the reaction sample 76, the reaction sample for detecting the presence of the target sequence is brought into contact with the matched probe and the mismatched probe. The matched probe and the mismatched probe brought into contact with the reaction sample can be immobilized on a microarray.

The reaction sample can be washed to eliminate any non-specific reactions in the optional washing operation, 77.

The occurrence of a hybridization reaction between the probes and a sequence in the sample is confirmed in the confirming of the hybridization reaction 78. Confirmation of the occurrence of hybridization is performed by detecting a fluorescence intensity and determining that the hybridization is realized when the intensity is above a standard value. Either a probe or a nucleic acid in the reaction sample can be labeled with a fluorophore, providing that the fluorophore alters its fluorescence emission upon formation of a hybrid between the probe and the nucleic acid. In some embodiments, each probe is labeled with a different fluorophore; with non-overlapping fluorescence spectra.

An example of measured fluorescence intensity with respect to each probe shown in FIG. 6 is illustrated in Table 1.

TABLE 1

| | pm #1 | mm #1 | pm #2 | mm #2 | pm #3 | mm #3 | pm #4 | mm #4 |
|---|---|---|---|---|---|---|---|---|
| Intensity | 10020 | 9479 | 5977 | 27259 | 5365 | 831 | 24911 | 9459 |

In Table 1, for example, when the fluorescence intensity is above 3000, hybridization is realized. In other words, it is determined as "ON." On the other hand, when the fluorescence intensity is less than or equal to 3000, hybridization is not realized. In other words, it is determined as "OFF."

In another embodiment, the fluorescence intensity cutoff for deter mining whether hybridization of the probe is "ON" or "OFF" is determined by the value calculated using Formula 4. When the value calculated using Formula 4 is above 3, hybridization is realized, i.e., "ON", and when the value calculated using Formula 4 is less than or equal to 3, hybridization is not realized, i.e., "OFF."

$$\log_2[(\text{fluorescence intensity of each probe})/(\text{background intensity})]$$ <Formula 4>

In Formula 4, the background intensity is the fluorescence intensity measured when a background reference sample, in which no nucleic acid is present, is brought into contact with the matched probe and the mismatched probe.

Table 2 illustrates an example of using Formula 4 to process the measured fluorescence intensity of each probe shown in FIG. 6.

TABLE 2

| | pm #1 | mm #1 | pm #2 | mm #2 | pm #3 | mm #3 | pm #4 | mm #4 |
|---|---|---|---|---|---|---|---|---|
| Log data | 3.47 | 3.54 | 4.21 | 3.02 | 2.32 | 3.42 | 2.92 | 3.74 |

As summarized in Table 3 below, when a value in Table 2 is above 3, "ON" is indicated and when a value of Table 2 is less than or equal to 3, "OFF" is indicated.

TABLE 3

| | pm #1 | mm #1 | pm #2 | mm #2 | pm #3 | mm #3 | pm #4 | mm #4 |
|---|---|---|---|---|---|---|---|---|
| Log data | ON | ON | ON | ON | OFF | ON | OFF | ON |

The presence of the target sequence is determined using the result indicating whether hybridization is realized or not in determining the presence of the target sequence, operation 79. Determining of the presence of the target sequence is performed by comparing the results obtained with the reaction sample, as illustrated above, with the results of hybridization of a reference sample containing the target sequence and no other nucleic acids.

Figure 8:
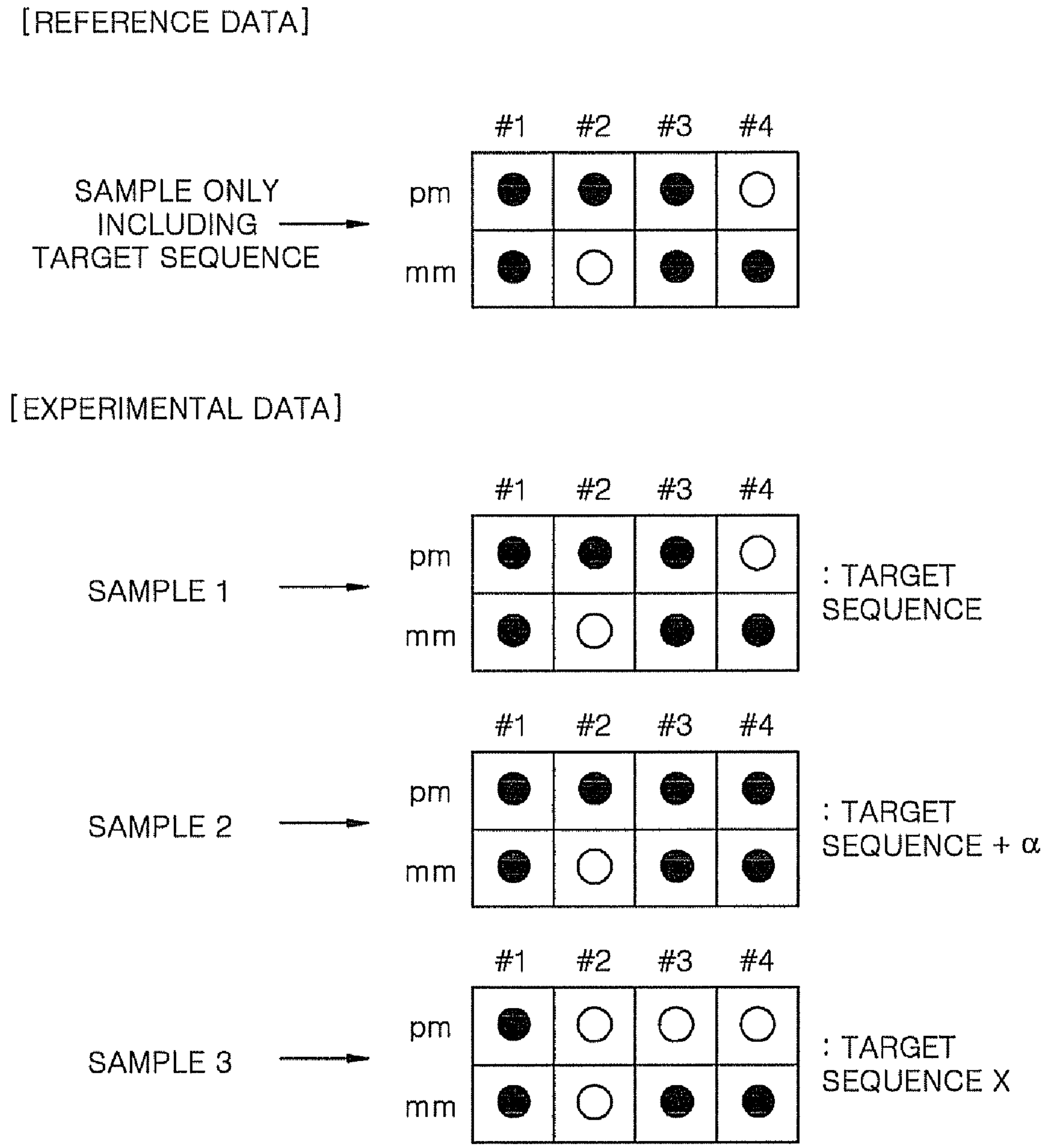
FIG. 8 is a schematic diagram illustrating an example of determining the presence of a target sequence according to an embodiment of the present invention.

FIG. 8 is a schematic diagram illustrating an example of determining the presence of the target sequence according to an embodiment of the present invention. The example of FIG. 8 uses a set of probes, such as the eight shown in FIG. 6, immobilized on a microarray in a 2×4 array conformation.

Referring to FIG. 8, reference samples only including the target sequence are provided to the microarray and then reference fluorescence data are obtained. In FIG. 8, a darkened spot represents high fluorescence intensity (i.e., above the cutoff value indicating occurrence of hybridization), whereas an open circle represents fluorescence intensity that is less than or equal to the cutoff value indicating occurrence of hybridization. In the reference data shown in FIG. 8, pm #1, pm #2, pm #3, mm #1, mm #3, and mm #4 indicate that hybridization is "ON."

Three different samples, each comprising potentially different nucleic acids, are tested with the same microarray as used above with the reference sample. The experimental data from sample 1 is the same as the reference data and therefore it is judged that the target sequence exists in sample 1.

In the experimental data obtained by using sample 2, the observed pattern of hybridization at the 8 microarray sites differs from that of the reference sample. For sample 2, pm #4 is "ON" in addition to probes pm #1, pm #2, pm #3, mm #1, mm #3, and mm #4 indicating "ON" in the reference sample data. Therefore, it is judged that sample 2 includes the target sequence and other sequences.

In the experimental data obtained by using sample 3, pm #1, mm #1, mm #3, and mm #4 are "ON." The experimental data of sample 3 at the 8 microarray sites is different from the reference data and thus it is judged that the target sequence is not included in sample 3.

The present invention will be described in greater detail with reference to the following examples. The following examples are for illustrative purposes and are not intended to limit the scope of the invention.

EXAMPLE 1

Designing Probes for Detecting a Target Sequence According to the Present Invention As illustrated in FIG. 6, 4 complete matched probes and 4 intended mismatched probes (SEQ ID NOs: 9 through 16) which can specifically detect a target sequence (SEQ ID NO: 1), a region of the 23S rRNA of *Streptococcus oralis* (sor), from non-target sequences (SEQ ID NOs: 2 through 8) were designed.

Sequences with SEQ ID NOs: 2 through 8 are corresponding regions of 23S-rRNA in *Streptococcus pneumoniae* (spn), *Streptococcus dysgalactia* (sgo), *Streptococcus pyogenes* (sdy), *Streptococcus sanguinis* (spo), *Streptococcus bovis* (ssu), *Streptococcus Gordonii* (sbo), and *Gemella melitensis* (gme). Each of these microorganisms is a species having similar sequences to the target sequence region (sequence no. 1) and to each other in the corresponding region of 23S rRNA, with SEQ ID NOs: 2-8) showing 1 bp or 2 bp variations from the target sequence (SEQ ID NO:1).

COMPARATIVE EXAMPLE 1

Designing Probes for Detecting a Target Sequence According to a Conventional Method As illustrated in FIG. 1, a probe (SEQ ID NO: 17) for detecting the target sequence (SEQ ID NO: 1) was designed using a conventional method.

EXPERIMENTAL EXAMPLE 1

Detecting the Target Sequence

Experimental Example 1 illustrates the difference between a conventional method and the method of using probes according to the present invention in detecting the target DNA in samples comprising the target DNA and DNAs having similar sequences to the target DNA. In the conventional method, one probe represented as the target sequence (SEQ ID NO: 1) is used. However, when samples comprising DNAs having similar sequences to each other are mixed, the presence of the target sequence cannot be accurately determined using a single probe.

The FIG. 6 probes (SEQ ID NO: 9 through 16) designed according to the present invention and the conventional probe (SEQ ID NO: 17) were used to confirm whether the target sequence can be specifically detected and the results were compared.

The experiment is performed by using the conventional method and the method of the present invention with respect to each of the following 16 samples:

Single DNA Samples:

DNA sample (sor) in which only SEQ ID NO: 1 were present;

DNA sample (spn) in which only SEQ ID NO: 2 were present;

DNA sample (sgo) in which only SEQ ID NO: 3 were present;

DNA sample (sdy) in which only SEQ ID NO: 4 were present;

DNA sample (ssu) in which only SEQ ID NO: 6 were present;

DNA sample (sbo) in which only SEQ ID NO: 7 were present;

DNA sample (gme) in which only SEQ ID NO:8 were present;

DNA Samples with a Mixture of any Two Samples Including:

DNA sample (spn+gme) in which SEQ ID NOS: 2 and 8 were mixed and present;

DNA sample (spn+sor) in which SEQ ID NO: 1 and SEQ ID NO: 2 were mixed and present;

DNA sample (spn+ssu) in which SEQ ID NO: 2 and SEQ ID NO: 6 were mixed and present;

DNA sample (gme+ssu) in which SEQ ID NO: 6 and SEQ ID NO: 8 were mixed and present;

DNA sample (sor+ssu) in which SEQ ID NO: 1 and SEQ ID NO: 6 were mixed and present;

DNA Samples with a Mixture of any Three Samples Including:

DNA samples (sor+spn+gme) in which SEQ ID NOS: 1, 2, and 8 were mixed and present;

DNA samples (spn+ssu+gme) in which SEQ ID NOS: 2, 6, and 8 were mixed and present;

DNA samples (spn+sor+ssu) in which SEQ ID NOS: 1, 2, and 6 were mixed and present; and DNA Samples with a Mixture of any Four Samples Including:

DNA sample (sor+spn+ssu+gme) in which SEQ ID NOS: 1, 2, 6, and 8 were mixed and present.

The results are shown in Table 4. In Table 4, the column 'samples' refers to the species of DNA present in the sample, as indicated by the designation in parentheses above in the description of the various samples tested.

The column 'correct' refers to the correct answer to be determined regarding the DNA present in the sample, based on sor (SEQ ID NO:1) as the target of detection. In other words, when the experiment is performed correctly, the result of the experiment should be the same as the result in the column 'correct'. When only the target DNA (sor, SEQ ID NO:1) is present in the sample, this is referred to in the "correct" column as sor. When sor is not present in the sample, this is referred to as non-sor. When sor and other DNA are present in the samples, this is referred to as sor+alpha.

In the column 'conventional method', detection of the presence of the target DNA (SEQ ID NO:1) is indicated with respect to each of the samples. Thus, whether the target DNA is detected correctly usinig the conventional method can be ascertained by comparing the results from the column 'conventional method' with those from the column 'correct'. For example, in the case of the first sample row, sor, the result of the experiment performed by using the conventional method is sor and since the correct result is sor, the presence of sequence no 1 is well detected from the sample in which only SEQ ID NO:1 is present. However, note that in sample row 2 (spn), the conventional method results in a false signal that SEQ ID NO:1 is present.

In the central section of Table 4, with the grid labeled with pm #1, pm #2, pm #3, pm #4, mm #1, mm #2, mm #3, and mm #4, respectively, these labels refer to probes used in the method according to the present invention. O and X in the appropriate spot of the grid in each sample row denote the results for each of the respective probes. An "O" indicates that the probe is hybridized above a threshold set for the probe and an "X" indicates that the probe is hybridized below the threshold set for the probe. In the present invention, detection of the presence of the target DNA is indicated by the hybridization pattern observed with the probes used in the method of the present invention. Analysis of the hybridization pattern detected for the grid of probes is as discussed above, with respect to FIG. 8.

In the column 'present invention', the result of the detection of the presence of the target DNA is summarized. In the first row, sor indicates that the target sequence, that is, SEQ ID NO:1, was detected as present in the sample.

The column 'Improvement' indicates whether the result of the present invention is better than that of the conventional method. For example, with respect to the sample spn in the second row, the correct result is non-sor. However, using the conventional method, sor was detected, that is, a false positive for the presence of the target sequence was observed. In the method using the probes of the present invention, non-sor was accurately detected. Thus, it can be ascertained that the detecting efficiency of the method of the present invention is improved over the conventional method using a single probe. In addition, when spn+gme+ssu were present in the sample in the 12th row of Table 4, the correct result was non-sor. However, in the conventional method, sor was again falsely detected as present in the sample. In the method using the probes of the present invention, non-sor was again accurately detected.

As illustrated in Table 4, the target sequence is accurately detected at the $11^{th}$ experiment among 16 experiments using the conventional method, and the target sequence is accurately detected at $15^{th}$ experiment using the method according to the present invention.

TABLE 4

| samples | correct | conventional method | pm #1<br>mm #1 | pm #2<br>mm #2 | pm #3<br>mm #3 | pm #4<br>mm #4 | present invention | improvement |
|---|---|---|---|---|---|---|---|---|
| sor | sor | sor | o | o | o | o | sor | |
| | | | o | o | o | x | | |
| spn | non − sor | sor | o | o | o | o | non − sor | improved |
| | | | o | o | x | x | | |
| sdy | non − sor | non − sor | x | x | x | o | non − sor | |
| | | | x | o | x | x | | |
| ssu | non − sor | non − sor | x | x | x | x | non − sor | |
| | | | x | x | x | x | | |
| sbo | non − sor | non − sor | x | x | x | x | non − sor | |
| | | | x | x | x | x | | |
| sgo | non − sor | non − sor | x | x | x | x | non − sor | |
| | | | x | x | x | x | | |
| gme | non − sor | non − sor | x | x | x | x | non − sor | |
| | | | x | x | x | x | | |
| spn + gme | non − sor | sor | o | x | o | o | non − sor | improved |
| | | | o | o | x | o | | |
| spn + sor | sor + alpha | sor | o | o | o | o | sor | |
| | | | o | o | o | x | | |
| spn + ssu | non − sor | sor | o | x | o | o | non − sor | improved |
| | | | o | o | x | x | | |
| spn + gme + sor | sor + alpha | sor | o | o | o | o | sor + alpha | |
| | | | o | o | o | o | | |
| spn + gme + ssu | non − sor | sor | o | x | x | o | non − sor | improved |
| | | | x | o | x | o | | |
| spn + sor + ssu | sor + alpha | sor | o | o | o | o | sor | |
| | | | o | o | o | x | | |
| spn + gme + sor + ssu | sor + alpha | sor | o | o | o | o | sor | |
| | | | o | o | o | x | | |

TABLE 4-continued

| samples | correct | conventional method | pm #1 mm #1 | pm #2 mm #2 | pm #3 mm #3 | pm #4 mm #4 | present invention | improvement |
|---|---|---|---|---|---|---|---|---|
| gme + ssu | non – sor | sor | ○ | ○ | ○ | ○ | non – sor | improved |
| | | | ○ | ○ | x | x | | |
| sor + ssu | sor + alpha | sor | ○ | ○ | ○ | ○ | non – sor | retrograded |
| | | | ○ | ○ | x | x | | |

According to the method of designing probes for detecting a target sequence of the present invention, probes can be designed to rapidly and accurately detect the presence of the target sequence in reaction samples containing the target sequence and a large number of non-target sequences.

In addition, according to the method of detecting target sequence of the present invention, the presence of the target sequence is rapidly and accurately detected in reaction samples containing the target sequence and a large number of non-target sequences.

The terminology used herein is for the purpose of describing particular embodiments only and is not intended to be limiting of the invention. The terms “a” and “an” do not denote a limitation of quantity, but rather denote the presence of at least one of the referenced item. The term “or” means “and/or”. The terms “comprising”, “having”, “including”, and “containing” are to be construed as open-ended terms (i.e., meaning “including, but not limited to”).

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., “such as”), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of selecting a pair of probe sequences for detecting a target sequence in a reaction sample comprising the target sequence and a plurality of non-target sequences, the method comprising:

selecting an anchoring location in a target sequence, wherein the anchoring location is a location in the target sequence at which a first non-target sequence in a plurality of non-target sequences is different from the target sequence, wherein the first non-target sequence has a sequence similarity to the target sequence that is identical to or higher than the sequence similarity of other non-target sequences in the plurality of non-target sequences;

selecting a first probe designing region in the target sequence, wherein the first probe designing region is a fixed region in the target sequence comprising the anchoring location, wherein the first probe designing region is represented by formula 1:

$$i-n+1 \leqq \text{first probe designing region} \leqq i+n-1 \qquad \text{formula 1}$$

wherein, i is the anchoring location and n is the length of a probe;

selecting a second probe designing region, wherein the second probe designing region is represented by formula 2 when the length of the probe is an odd number and by formula 3 when the length of the probe is an even number:

$$i-(n-1)/2 \leqq \text{second probe designing region} \leqq i+(n-1)/2; \qquad \text{formula 2}$$

$$i-n/2+1 \leqq \text{second probe designing region} \leqq i+n/2-1; \qquad \text{formula 3}$$

identifying a location in the second probe designing region of the target sequence at which a second non-target sequence in the plurality of non-target sequences differs from the target sequence;

selecting the identified location as a probe selection location;

selecting a matched probe sequence, wherein the probe selection location is at the center of the matched probe sequence; and selecting a mismatched probe sequence, wherein the mismatched probe sequence is longer than the matched probe sequence, wherein the probe selection location is at a first location in the mismatched probe sequence and the mismatched location is at a second location in the mismatched probe sequence, wherein the steps are executed by a suitably programmed computer.

2. The method of claim 1, wherein if multiple non-target sequences in the plurality have a sequence similarity to the target sequence which is the highest sequence similarity present in the plurality, and if the locations at which each non-target sequence with the highest sequence similarity differs from the target sequence are different, then the anchoring location is any one of the locations.

3. The method of claim 1, wherein if multiple non-target sequences have the highest sequence similarity to the target sequence can be grouped based on the location of difference with the target sequence and there are 2 or more groups, then the anchoring location is selected to be the location of the group having highest frequency of occurrence.

4. The method of claim 1, wherein if multiple non-target sequences have the highest sequence similarity to the target sequence can be grouped based on the location of difference with the target sequence and there are 2 or more groups, and each group has the same frequency, then the anchoring location is any one of the locations.

5. The method of claim 1, wherein when a length of the matched probe sequence (n) is an odd number, the center of the matched probe sequence is at a (n+1)/2 th position in the matched probe sequence, and when the length of the matched probe sequence (n) is an even number, the center of the matched probe sequence is at a n/2 th or n/2+1 th position in the matched probe sequence.

6. The method of claim 1, wherein the first location is at ⅓ of a length of the mismatched probe sequence, and the second location is at ⅔ of the length of the mismatched probe sequence.

7. The method of claim 6, wherein for the mismatched probe sequence of length m, if the length of the mismatched probe sequence is a multiple of 3, the locations corresponding to ⅓ and ⅔ of the length of the mismatched probe sequence are at m/3th and 2m/3+1 th positions, respectively;

if the length of the mismatched probe sequence m is a multiple of 3+1, the locations corresponding to ⅓ and ⅔ of the length of the mismatched probe sequence are at descending order of m/3 and (descending value of m/3)×2+1 th positions, respectively or (descending value of m/3)+1 st and (descending value of m/3)×2+2th positions, respectively; and if the length of the mismatched probe sequence m is a multiple of 3+2, the locations corresponding to ⅓ and ⅔ of the length of the mismatched probe sequence are at (descending value of m/3)+1 st and (descending value of m/)×2+2 nd positions, respectively.

8. The method of claim 1, wherein a length of the matched probe sequence is 17 to 25 bp and a length of the mismatched probe sequence is 25 to 36 bp.

9. A method of detecting a target sequence, the method comprising:

contacting a sample comprising nucleic acid with a matched probe and a mismatched probe having the matched probe sequence and the mismatched probe sequence selected by the method of claim 1;

detecting hybridization between the matched probe or the mismatched probe and nucleic acid present in the sample; and determining the presence or absence of the target sequence in the sample by comparing the detected hybridization with hybridization of a reference sample containing only the target sequence.

10. The method of claim 9, wherein the matched probe and the mismatched probe are immobilized on a microarray substrate.

11. The method of claim 10, further comprising after the step of contacting the sample with the matched probe and the mismatched probe:

washing the microarray substrate.

12. The method of claim 9, wherein detecting hybridization comprises detecting a fluorescence intensity; and determining that hybridization occurred if the fluorescence intensity is above a fixed value.

13. A computer readable storage medium having recorded thereon a program for causing a computer to perform the method according to claim 1.

* * * * *